United States Patent [19]

Spivack

[11] 4,288,391

[45] * Sep. 8, 1981

[54] ALKYLATED 2,2'-BIPHENYLENE PHOSPHITES

[75] Inventor: John D. Spivack, Spring Valley, N.Y.

[73] Assignee: Ciba-Geigy Corporation, Ardsley, N.Y.

[*] Notice: The portion of the term of this patent subsequent to Apr. 1, 1997, has been disclaimed.

[21] Appl. No.: 93,786

[22] Filed: Nov. 13, 1979

Related U.S. Application Data

[63] Continuation-in-part of Ser. No. 866,748, Jan. 3, 1978, Pat. No. 4,196,117.

[51] Int. Cl.$^3$ .................................................. C07F 9/15
[52] U.S. Cl. .................................. 260/927 R; 260/936
[58] Field of Search ........................... 260/927 R, 936

[56] References Cited

U.S. PATENT DOCUMENTS

| | | | |
|---|---|---|---|
| 3,297,631 | 1/1967 | Bown et al. | 260/45.95 D |
| 3,415,906 | 12/1968 | Shepard et al. | 260/937 |
| 3,476,699 | 11/1969 | Kauder et al. | 260/23 |
| 3,558,554 | 1/1971 | Kuriyama et al. | 260/45.85 R |
| 3,796,684 | 3/1974 | Dever et al. | 260/45.8 R |
| 4,094,855 | 6/1978 | Spivack | 260/45.8 NT |
| 4,196,117 | 4/1980 | Spivack | 260/936 |

OTHER PUBLICATIONS

Abstract of USSR 274,293, from Soviet Inventions Illustrated, 1/1971.
Verizhnikov, et al., "Chem. Abs.", vol. 68, (1968), 12597s.
Kirpichnikov, et al., "Chem. Abs.", vol. 73, (1970) 15657a.
Verizhnikov, et al., "Chem. Abs.", vol. 75 (1975), 130242a.
Derwent Abstract of Russian Pat. Nos. 378,389, 429,070, 440,390.

*Primary Examiner*—Anton H. Sutto
*Attorney, Agent, or Firm*—Luther A. R. Hall

[57] ABSTRACT

Alkylated 1,1'-biphenyl-2,2'diyl phosphites are prepared by reacting alkylated 2,2'-biphenol with phosphorous trichloride in an organic solvent and then reacting the intermediate with an alcohol or thiol. Said phosphites are useful as stabilizers of organic polymers and lubricating oils, especially as process stabilizers for polyolefins, elastomers, polyesters and polycarbonates.

8 Claims, No Drawings

ALKYLATED 2,2'-BIPHENYLENE PHOSPHITES

This is a continuation-in-part of application Ser. No. 866,748, filed Jan. 3, 1978, now U.S. Pat. No. 4,196,117, issued Apr. 1, 1980.

BACKGROUND OF THE INVENTION

Organic polymeric materials such as plastics and resins and lubricating and mineral oil are subject to thermal, oxidative and photodegradation. A great variety of stabilizers are known in the art for stabilizing various substrates. Their effectiveness varies depending on the causes of degradation and the substrate stabilized. During the course of this work, it was discovered that stabilizers that are very effective long term antioxidants are relatively poor process stabilizers which require stabilization of the substrate against thermal degradation for a short time, but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers. The prior art discloses unhindered 2,2'-biphenylenephenylphosphite and 2,2'-methylene bis(dialkylphenyl) phenylphosphites (Chem. Abst. 68, 12597q (1968), Chem. Abst. 73, 15657a (1970), Chem. Abst 75, 130242q (1971) and Soviet Union Pat. Nos. 378,389 and 429, 070). These compounds are said to be stabilizers of various polymers. However, the phosphites of this invention are much more effective especially as process stabilizers for polyolefins and other substrates, both in prevenging polymer chain scission as well as discoloration during high temperature processing.

DETAILED DISCLOSURE

This invention is directed to alkylated 1,1'-biphenyl-2,2'-diyl phosphites and to polymeric and non-polymeric organic materials stabilized with said phosphites. More specifically the phosphites of this invention can be represented by the formula

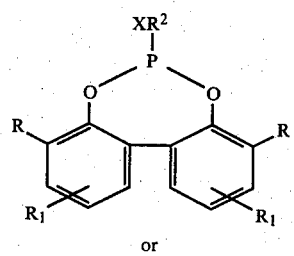

or

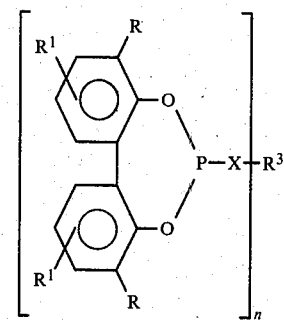

wherein
R is an alkyl group of 1 to 18 carbon atoms,
$R^1$ is hydrogen or an alkyl group of 1 to 18 carbon atoms, and
$R^2$ is an alkyl group of 1 to 20 carbon atoms, phenyl, phenyl substituted by 1 to 3 alkyl groups each having 1 to 8 carbon atoms or by two alkyl groups each having 1 to 8 carbon atoms and by $-COOR^4$ where $R^4$ is alkyl of 1 to 18 carbon atoms,
$R^3$ is an n-valent radical selected from the group consisting of a straight- or branched-chain alkylene of 2 to 12 carbon atoms, a straight- or branched-chain alkane-triyl, -tetrayl, -pentayl or -hexayl of 3 to 6 carbon atoms, alkenylene of 4 to 6 carbon atoms, cycloalkylene of 6 to 12 carbon atoms, 1,4-cyclohexanedimethylene, arylene or arenetriyl of 6 to 10 carbon atoms, p-xylylene, phenylene —E— phenylene where E is a direct bond, —O—, —S—, —NR$^5$—, where $R^5$ is alkyl of 1 to 18 carbon atoms; a straight- or branched-chain alkylene or alkylidene of 1 to 12 carbon atoms or cycloalkylidene of 5 to 6 carbon atoms, said arylene or said phenylene-E-phenylene substituted by 1 to 4 alkyl groups each having 1 to 8 carbon atoms, $-(CH_2)_xS(CH_2)_x-$ where x is 2 to 6, dipentaerythrityl, and

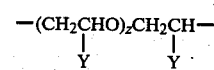

where Y is hydrogen, methyl or ethyl and z is 1 to 10,
X is oxygen or sulfur, and
n is 2 to 6.

The R groups are preferably straight-chain or branched alkyl with 1-8 carbon atoms, such as methyl, ethyl, n-propyl, iso-propyl, n-butyl, sec.-butyl, tert.-butyl, 2-ethylhexyl, n-octyl or tert-octyl. α-Branched alkyl radicals with 3-8 carbon atoms are more preferred. The groups tert-butyl and tert-octyl are especially preferred. Also especially it is preferred for the $R^1$ group to be in the para position to oxygen, particularly if $R^1$ is tert.-alkyl.

Although $R^1$ can be hydrogen or alkyl of 1 to 18 carbons, preferably it is an alkyl group of 1 to 8 carbon atoms, either straight-chain or branched-chain. Especially preferred is tert.-alkyl of 4 to 8 carbon atoms.

The group $R^2$ can be alkyl of 1 to 20 carbon atoms, such as methyl, ethyl, butyl, hexyl, heptyl, octyl, decyl, dodecyl, octadecyl, eicosyl and the like; or it can be phenyl or alkyl substituted phenyl, such as tolyl, xylyl, mesitylyl, ethylphenyl, butyl-phenyl, 3,5-dibutylphenyl, p-octyl-phenyl, 3,5-dioctylphenyl and the like. Preferably $R^2$ is a phenyl group having at least one branched alkyl group. Most preferably $R^2$ is 2-tert-butylphenyl, 2,4-di-tert-butyl-phenyl, 2,4,6-tri-tert-butylphenyl, 2-tert-butyl-5-methylphenyl, 2,6-di-tert-butyl-phenyl and 2,6-di-tert-butyl-4-methylphenyl, and 2,4-di-tert-octylphenyl.

$R^2$ can also be phenyl substituted by two alkyl groups each having 1 to 8 carbon atoms and by —COOR$^4$ where $R^4$ is alkyl of 1 to 18 carbon atoms. Preferably $R^2$ is phenyl substituted in the ortho positions by two alkyl groups each having 3 to 8 carbon atoms and in the para-position by —COOR$^4$ where $R^4$ is alkyl of 1 to 12 carbon atoms. Most preferably $R^2$ is phenyl substituted in the ortho positions by two tert-butyl groups and in the para position by carbomethoxy where $R^4$ is methyl.

When $R^3$ is a straight or branched chain alkylene, alkanetriyl, alkanetetrayl, alkanepentayl or alkanehexayl, it may be ethylene, 1,2-propylene, trimethylene, tetramethylene, hexamethylene, dodecomethylene, 1,2,3-propanetriyl, 2,2-dimethyl-1,2,2-propanetriyl, pentaerythrityl, 1,2,3,4,5,6-hexanehexayl and the like. Preferably $R^3$ is alkylene of 2 to 6 carbon atoms, 1,2,3-propanetriyl, 2,2-dimethyl-1,2,2-propanetriyl and pentaerythrityl.

$R^3$ may also be alkenylene of 4 to 6 carbon atoms such as 2-butene-1,4-diyl or 3-hexene-2,5-diyl.

$R^3$ may also be cycloalkylene of 6 to 12 carbon atoms such as 1,2-, 1,3- or 1,4-cyclohexylene, 1,5-cyclooctylene or 1,2-cyclododecylene.

Preferably $R^3$ as cycloalkylene is cyclohexylene and most preferably 1,4-cyclohexylene. $R^3$ is also preferably 1,4-cyclohexanedimethylene.

$R^3$ can also be arylene or arenetriyl of 6 to 10 carbon atoms such as 1,2-, 1,3- or 1,4-phenylene, 1,2,3-, 1,2,4- or 1,3,5- benzenetriyl, or 1,3-, 1,5-, 1,7-, 2,3-, 2,6- or 2,7-naphthylene. Preferably $R^3$ as arylene is phenylene and most preferably is 1,4-phenylene.

$R^3$ is also phenylene-E-phenylene preferably where the phenylene rings are each 1,4-phenylene groups. E is a direct bond, —O—, —S—, —NR$^5$— where $R^5$ is alkyl of 1 to 18 carbon atoms or is a straight- or branched-chain alkylene or alkylidene of 1 to 12 carbon atoms such as methylene, ethylidene, 2,2-propylidene, 1,1-butylidene, 1,1-hexylidene or 1,1-dodecylidene. E may also be cyclo-alkylidene of 5 to 6 carbon atoms such as 1,1-cyclopentylidene or 1,1-cyclohexylidene, preferably 1,1-cyclohexylidene. Preferably when $R^3$ is phenylene-E-phenylene, E is methylene, 2,2-propylidene or 1,1-butylidene.

$R^3$ can be arylene or phenylene-E-phenylene where the arylene or phenylene is substituted with 1 to 4 alkyl groups each alkyl having 1 to 8 and preferably 1 to 4 carbon atoms. Illustrative examples of arylene groups are phenylene, tolylene, 1,3,5-tri-methyl-phenylene, 1,2,4,5-tetramethylphenylene; 2,5-tert-butyl-phenylene, 2,6-di-tert-butylphenylene, or the like.

$R^3$ may also be —(CH$_2$)$_x$S(CH$_2$)$_x$— where x is 2 to 6, preferably where each x is 2 so that $R^3$ is 3-thiapentamethylene.

$R^3$ can also be

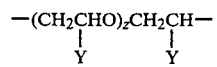

where Y is hydrogen, methyl or ethyl, preferably hydrogen or methyl and most preferably hydrogen. z is an integer from 1 to 10, preferably 1 to 3.

The alkylated 1,1'-biphenyl-2,2'-diyl phosphites of this invention can be prepared by reacting an alkylated 2,2'-biphenol with phosphorus trichloride in a solvent to give the corresponding phosphorochloridite which in turn is reacted with an alkali metal alcoholate or phenolate to yield the desired product. The solvent is preferably aromatic, such as benzene, toluene, xylene and the like. A reaction temperature from room temperature to the reflux temperature of the reaction medium. Another method for preparing the compounds of this invention involves reacting the phosphorochlordite with an appropriate alcohol or phenol optionally in the presence of a proton accceptor such as a tertiary amine, for example, triethylamine or pyridine.

The starting materials needed to prepare these phosphites are items of commerce or can be prepared by known methods.

The compounds of this invention are effective light stabilizers and/or antioxidants in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene, with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methyl acrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polyisobutylene oxide.

13. Polyphenylene oxides.

14. Polyurethanes and polyureas.

15. Polycarbonates.

16. Polysulphones.

17. Polyamides and copolyamides which are derived from diamines and dicarboxylic acids and/or from aminocarboxylic acids for the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.

19. Cross-linked polymers which are derived from aldehydes on the one hand and from phenols, ureas and melamines on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

Compounds of this invention are particularly effective in stabilizing organic materials such as plastics, polymers, resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers. Also stabilized are polyurethanes, polycarbonates, polyamides such as nylon 6, 6/6 and the like as well as copolyamides and polysulfones.

The compounds oif this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutyleneterephthalates, polycarbonates, natural rubber, synthetic rubber such as SBR. While many compounds which have been used as process stabilizers are sufficiently effective as process stabilizers for polyolefins only in the presence of costabilizers such as phenolic antioxidants, compounds of this invention are effective in the absence of phenolic antioxidants.

Many of the compounds of this invention combine process stabilizing properties with the ability to confer light stability on the polymer. This is particularly for polymer fibers where processing temperatures are among the highest and where stability to actinic light is a prime requirement. A particularly important property for stabilizers which are trivalent phosphorus esters is their nonhygroscopicity and resistance to hydrolysis in the presence of moisture in the atomsphere during ambient storage. Hygroscopicity frequently results in difficulty in incorporating the process stabilizer uniformly into the polymer causing stickiness and blockage during compounding, while hydrolysis of the phosphorus ester stabilizers during storage frequently results in compounds which are less effective.

The stabilizers of Formula I may readily be incorporated into the organic polymers by conventional techniques, at any conventient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Deratives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6(α-methylcyclohexyl)-phenol], 1,1-bis-(3,5-dimethyl-2-hydroxyphenyl)butane, 1,1-bis-(5-tert.-butyl-4-hydroxy-2-methylphenyl)-butane, 2,2-(5-tert.-butyl-4-hydroxy-2-methylphenyl)-propane, 1,1,3-tris(5-tert-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxy-anilino)-s-triazine, 2-octylmercapto-4,6-bis-(3,5-di-tert.-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)hexamethylene-diamine. N,N'-bis-β-(3,5-di-t-butyl-4-hydroxyphenyl)-propionyl)-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11 Esters of β-(5-tert.-butyl-4-hydroxy-3-methylphenyl propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, tri-methylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13 Benzylphosphonates, such as, for example, dimethyl 3,5-di-tert.-butyl-4-hydroxybenzyl-phosphonate, diethyl 3,5-di-tert.-butyl-4-hydroxybenzyl-phosphonate, dioctadecyl 3,5-di-tert.-butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g.

Phenyl-1-naphthylamine, phenyl-2-naphthalamine, N,N'-di-phenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctylimiodibenzyl, polymerized 2,2,4-trimethyl-1,2-dihydroquinoline Octylated diphenylamine, nonylated diphenylamine, N-phenyl-N'-cyclohexyl-p-phenylenediamine, N-phenyl-N'-isopropyl-p-phenylenediamine, N,N'-di-sec.-octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamine-acetone condensation product, aldol-1-naphthylamine and phenothiazine.

Discoloration effects have to be taken into account when using the above antioxidants.

2. UV-Absorbers and light-stabilizing agents 2.1 2-(2'-Hydroxyphenyl)-benzotriazoles, e.g. the 5'-methyl-, 3',5'-di-tert.-butyl-, 5'-tert.-butyl-,5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl, 3'-α-methylbenzyl-5'-methyl-, 3'-α-methylbenzyl-5'-methyl-5-chloro-,4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2 2,4-bis(2'-Hydroxyphenyl)-6-alkyl-s-triazines, e.g. the 6-ethyl-, 6-heptadecyl- or 6-undecyl-derivative.

2.3 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivatives.

2.4 1,3-bis-(2'-Hydroxybenzoyl)-benzenes, e.g. 1,3-bis(2'-hydroxy-4'-hexyloxy-benzoyl)-benzene, 1,3-bis-hydroxy-4'-octyloxy-benzoyl)-benzene or 1,3-bis-(2'-hydroxy-4'-dodecyloxybenzoyl)-benzene.

2.5 Esters of optionally substituted benzoic acids, e.g. phenylsalicylate, octylphenylsalicylate, dibenzoylresorcin, bis-(4-tert.butylbenzoyl)-resorcin, benzoylresorcin, 3,5-di-tert.butyl-4-hydroxybenzoic acid-2,4-di-tert.-butylphenyl ester or -octadecyl ester or -2-methyl-4,6-di-tert.-butyl ester.

2.6 Acrylates, e.g. α-cyano-β,β-diphenylacrylic acid-ethyl esters or -isooctyl ester, α-carbomethocy-cinnamic acid methyl ester, α-cyano-β-methyl-p-methoxycinnamic acid methyl ester or -butyl ester or N-(β-carbomethoxyvinyl)-2-methyl-indoline.

2.7 Sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,2,8-triaza-spiro[4,5]-decane-2,4-dione.

2.8 Oxalic acid diamides, e.g. 4,4'-di-octyloxy-oxanilide, 2,2'-di-octyloxy-5,5'-di-tert.-butyl-oxanilide, 2,2'-didodecyloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicycloylhydrazine, N,N'-bis-(3,5-di-tert.butyl-4-hydroxyphenylpropionyl)-hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilizers, e.g. alkali metal salts and alkaline earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri(nonylphenyl) phosphite, trilauryl phosphite, trioctadecyl phosphite, 3,9-isodecyloxy-2,4,8,10-tetraoxa-3,9-diphospha[5,5]-undecane and tri-(4-hydroxy-3,5-di-tert.-butylphenyl) phosphite.

Other additives that can be incorporated in the stabilized compositions are thiosynergists such as dilauryl thiodiproprionate or distearyl thiodipropionate, lubricants such as stearyl alcohol, fillers, carbon black, asbestos, kaolin, talc, glass fibers, pigments, optical brighteners, flameproofing agents and antistatic agents.

While the instant phosphites can be beneficially used as stabilizers for a variety of substrates, particularly the polyolefins, both alone and in conjunction with other coadditives, the combination of the instant phosphites with selected hindered phenolic antioxidants exhibits enhanced and particularly salubrious protection to such substrates. The phenolic antioxidants found to be particularly useful are selected from the group consisting of 2,6-di-tert-butyl-4-methylphenol, 4,4'-thio-bis(6-tert-butyl-3-methylphenol), 2,2'-mehtylene-bis(6-tert-butyl-4-methylphenol), 4,4'-methylene-bis-(2,6-di-tert-butylphenol), 1,1,3-tris(5-tert-butyl-4-hydroxy-2-methylphenyl)butane, 1,3,5-tris(3,5-di-tert-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis(3,5-di-tert-butyl-4-hydroxyhydrocinnamate), 1,3,5-tris(3,5-di-tert butyl-4-hydroxybenzyl) isocyanurate and thiodiethylene bis(3,5-di-tert-butyl-4-hydroxyhydrocinnamate).

The compositions comprise (a) a substrate, preferably a polyolefin such as polypropylene, (b) about 0.01 to about 5% by weight of the composition, preferably about 0.025 to about 2% and most preferably 0.025 to 1%, of an instant phosphite compound or mixture thereof, and (c) a phenolic antioxidant or mixture of said antioxidants selected from the group cited directly above and also in a range of 0.01 to 5%, preferably 0.05 to 1%, by weight of the composition.

EXAMPLE 1

Preparation of (3,3',5,5'-tetra-tert.-butyl-1,1'-biphenyl-2,2'diyl) phosphorochloridite 45.21 grams of phosphorous trichloride in 50 ml of toluene was added dropwise over 85 minutes to a solution of 123.0 grams of 4,4',6,6'-tetra-tert.-butyl-2,2'-biphenol and 60.6 grams of triethylamine in about 600 ml of toluene and stirred at room temperature overnight (about 20 hours). The reaction product was filtered free of triethylamine hydrochloride, the desired product being isolated by removal of the solvent at reduced pressure to yield a solid m.p. 168°–174°.

| Analysis | % Cl |
|---|---|
| Calcd. | 7.46 |
| Found | 7.50 |

EXAMPLE 2

O-(2,4-di-tert.-butylphenyl)O$^1$, O$^2$-(3,3',5,5'-tetra-tert.butyl-1,1'-biphenyl-2,2'diyl) phosphite 4.85 grams of 46.3% aqueous potassium hydroxide was added to a solution of 8.24 grams of 2,4-di-tert.-butylphenol in 250 ml of toluene and heated at reflux over a period of about 2 hours until all the water including reaction water was removed by azeotropic distillation yielding a dispersion of the potassium 2,4-di-tert. butylphenolate in toluene. To this dispersion at −5° C. was added a solution of 21.7 grams of the compound of Example 1 in 60 ml of toluene at −5° to −3° C. over a period of 25 minutes and then stirring continued overnight. The reaction mixture was clarified by filtration of the precipitated potassium chloride and the product isolated as a residue by distillation of the toluene at reduced pressures. The product was isolated as crystals after crystallization from a solvent mixture of acetonitrile and toluene yielding white crystals melting at 195°–197° C.

| Analysis | % C | % H |
|---|---|---|
| Calcd. | 78.22 | 9.53 |
| Found | 78.56 | 9.86 |

EXAMPLE 3

O-(2,4-di-tert.-butyl-4-methylphenyl)-O$^1$,O$^2$-(3,3',5,5'-tetra-tert.-butyl-1,1'-biphenyl-2,2'-diyl) phosphite The compound of this example was made by substantially the same method as Example 2 by reacting (3,3,',5,5'-tetra-tert.-butyl-1,1'-biphenylene-2,2'-diyl)-phosphorochlorodite with potassium 2,6-di-tert.-butyl-4-methylphenolate. After crystallization, the product is obtained as white crystals melting at 151°–155° C.

EXAMPLE 4

O-(2,4,6-tri-tert.-butylphenyl)-O$^1$,O$^2$-(3,3',5,5'-tetra-tert.-butyl-1,1'-biphenyl-2,2'diyl) phosphite The compound of this example was made by substantially the same method as Example 2 by reacting (3,3',5,5'-tetra-tert.-butyl-1,1'-biphenyl-2,2'-diyl) phosphorochlorodite with potassium 2,4,6-tri-tert.-phenolate. After crystallization, the product is obtained as white crystals melting at 210°–212° C.

EXAMPLE 5

O-Isopropyl-O$^1$,O$^2$-(3,3',5,5'-tetra-tert.-butyl-1,1'-biphenyl-2,2'-diyl) phosphite A solution of 23.75 grams of the chloridite of Example 1 in 80 ml of toluene was added dropwise at 15°–20° C. to 3.0 grams of isopropanol dissolved in 50.5 grams of triethylamine and stirring continued overnight at room temperature. After being filtered free of triethylamine hydrochloride and removal of volatiles at reduced pressures, the resulting residue was crystallized from isopropanol yielding the product as white crystals melting at 154°–156° C.

| Analysis | % C | % H |
|---|---|---|
| Calcd. | 74.66 | 9.42 |
| Found | 74.34 | 9.73 |

EXAMPLE 6

S,S'-(Trimethylene)bis-(O,O'(3,3',5,5'-tetra-tert.-butyl-1,140-biphenyl-2,2'-diyl) thiophosphite)

The compound of this Example was made by the same procedure as Example 5 by reacting two molar proportions of tetra-3,3',5,5'-tert.-butyl-1,1'-biphenyl-2,2'-diyl phosphorochloridite (Example 1) with one molar proporrtion of 1,3-propanedithiol in the presence of triethylamine. After crystallization the product melted at 190°–193° C.

EXAMPLE 7

O,O'(methylene-bis-(2,6-di-tert.-butylphenylene))-O$^1$,O$^2$-((3,3',5,5'-tetra-tert.-butyl-1,1'-biphenyl-2,2'diyl)-phosphite)

The compound of this example is made by the same procedure as Example 5 by reacting two molar proportions of the chloridite of Example 4 with the one molar proportion of 4,4'-methylene-bis(2,6-di-tert.-butylphenol) in the presence of triethylamine.

EXAMPLE 8

O-n-octadecyl-O$^1$,O$^2$-(3,3',5,5'-tetra-tert-butyl-1,1'-biphenyl-2,2'-diyl) phosphite The compound of this example was made by substantially the same procedure as Example 5 by reacting equimolar quantities of the chloridite of Example 1 with n-octadecanol in the presence of triethylamine. After purification by chromatography and by crystallization the product was obtained as white crystals melting at 38°–41° C.

Following the procedure of Example 5, the following compounds are prepared by reacting the appropriate starting materials.

| Ex. No. | R | R$^1$ | X | R$^2$ of R$^3$ | n |
|---|---|---|---|---|---|
| 9 | (CH$_3$)$_3$C— | 4-(CH$_3$)$_3$C— | O | CH$_3$—<br>mp = 190-192° C. | — |
| 10 | C$_8$H$_{17}$— | 4-CH$_3$— | O | C$_{18}$H$_{37}$— | — |
| 11* | (CH$_3$)$_3$C— | 4-(CH$_3$)$_3$C— | O | t-C$_4$H$_9$–⟨Ph⟩–COOCH$_3$ (t-C$_4$H$_9$)<br>mp = 255-258° C. | — |
| 12 | (CH$_3$)$_3$C— | 5-CH$_3$— | O | C$_8$H$_{17}$— | — |
| 13 | (CH$_3$)$_3$C— | 4-(CH$_3$)$_3$C— | O | t-C$_4$H$_9$,t-C$_4$H$_9$–⟨Ph⟩–CH$_2$–⟨Ph⟩– t-C$_4$H$_9$,t-C$_4$H$_9$ | 2 |
| 14 | (CH$_3$)$_3$C— | 4-(CH$_3$)$_3$C— | O | —⟨Ph⟩—C(CH$_3$)$_2$—⟨Ph⟩— | 2 |
| 15** | (CH$_3$)$_3$C— | 4-CH$_3$)$_3$C— | O | —CH$_2$C(CH$_3$)$_2$CH$_2$— | 2 |

-continued

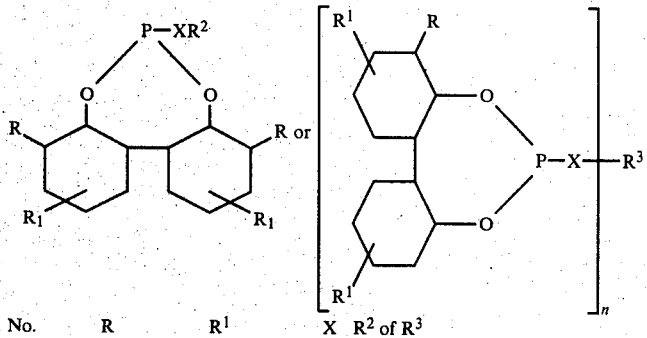

| Ex. No. | R | R¹ | X | R² of R³ | n |
|---|---|---|---|---|---|
| 16 | (CH₃)₃C— | 4-(CH₃)₃C | S | C₈H₁₇—  mp = 200–202° C. | — |
| 16a | t-C₄H₉ | 4-t-C₄H₉ | O | —(CH₂)₆—  mp = 181–183° C. | 2 |
| 16b | t-C₄H₉ | 4-t-C₄H₉ | O | neopentyl  mp = 151–153° C. | — |
| 16c | t-C₄H₉ | 4-t-C₄H₉ | O | isobutyl  mp = 148–150° C. | — |
| 16d | t-C₄H₉ | 4-t-C₄H₉ | O | 2-ethylhexyl  mp = 77–81° C. | — |
| 16e | t-C₄H₉ | 4-CH₃ | O | —(CH₂)₄— | 2 |
| 16f | t-C₄H₉ | 4-CH₃ | O | eicosyl | — |
| 16g | t-C₄H₉ | 4-t-C₄H₉ | O | 1,4-cyclohexylene | 2 |
| 16h | t-C₄H₉ | 4-t-C₄H₉ | O | —(CH₂CHO)₂CH₂CH—                  \|         \|                 CH₃   CH₃ | 2 |
| 16i | t-C₄H₉ | 4-t-C₄H₉ | O | 3-thiapentamethylene | 2 |
| 16j | t-C₄H₉ | 4-t-C₄H₉ | O | pentaerythrityl | 4 |
| 16k | t-C₈H₁₇ | 4-t-C₄H₉ | O | hexanehexayl | 6 |

*The alcohol was methanol with the chloridite:alcohol ratio of 1:1.
**The alcohol used was 2,2-dimethyl-1,3-propanediol with the chloridite:alcohol ratio of 2:1.

EXAMPLE 17

Processing Stability of Polypropylene at 500° F.

| Base Formulation: | |
|---|---|
| Profax 6801 | 100 parts |
| Calcium stearate | 0.10 parts |

Stabilizers were solvent blended into polypropylene as solutions in methylene chloride and, after removal of the solvent by evaporation at reduced pressure, the resin was extruded using the following extruder conditions:

| | Temperature | |
|---|---|---|
| | (°F.) | (°C.) |
| Cylinder #1 | 450 | 232 |
| Cylinder #2 | 475 | 246 |
| Cylinder #3 | 500 | 260 |
| Die #1 | 500 | 260 |
| Die #2 | 500 | 260 |
| RPM | 100 | |

During extrusion, the internal extruder pressure was determined using a pressure transducer. After each of the first, third and fifth extrusions, resin pellets were compression molded into 125 mil (3.2 mm) thick plaques at 380° F. (193° C.) and specimen yellowness index (Y.I.) determined according to ASTM D1925-63T.

The melt flow rate (MFR) was determined by ASTM method 1238 condition L. The melt flow rate varies directly as the transducer pressure and both are a measure of the molecular weight for a specific type of polymer. The data is presented in Table I below:

TABLE 1

| Additive | (psi) Transducer Pressure After Ext. | | | ** MFR (g/10 min) After Ext. | | | YI Color*** After Extrusion | | |
|---|---|---|---|---|---|---|---|---|---|
| | 1 | 3 | 5 | 1 | 3 | 5 | 1 | 3 | 5 |
| None | 1095 | 840 | 655 | 0.73 | 2.01 | 4.25 | 4.6 | 6.5 | 7.9 |
| 0.1 Antiox. A* | 1215 | 1045 | 930 | 0.42 | 1.04 | 1.25 | 6.7 | 8.6 | 10.5 |
| 0.15 Antiox. A* | 1270 | 1110 | 990 | 0.40 | 0.40 | 1.06 | 7.8 | 10.3 | 12.5 |
| The following contain 0.1% Antioxidant A and a compound as indicated below: | | | | | | | | | |
| 0.05 Cmpd. Ex. 2 | 1260 | 1125 | 1035 | | | | 5.9 | 7.4 | 9.9 |
| 0.05 Cmpd. Ex. 3 | 1250 | 1080 | 1020 | | | | 5.9 | 8.0 | 9.3 |
| 0.05 Cmpd. Ex. 4 | 1230 | 1120 | 1010 | | | | 6.1 | 8.6 | 10.3 |
| 0.05 Cmpd. Ex. 5 | 1380 | 1275 | 1200 | | | | 4.8 | 6.1 | 7.8 |
| 0.05 Cmpd. Ex. 8 | 1350 | 1260 | 1170 | | | | 5.3 | 7.1 | 9.0 |

TABLE 1-continued

| 0.05 | Cmpd. | Ex. 9  | 1335 | 1260 | 1200 | 0.19 | 0.24 | 0.36 | 5.4 | 6.6 | 8.5 |
| 0.05 | Cmpd. | Ex. 6  | 1335 | 1260 | 1230 | 0.19 | 0.25 | 0.34 | 5.9 | 6.7 | 8.2 |
| 0.05 | Cmpd. | Ex. 15 | 1375 | 1275 | 1230 | 0.20 | 0.24 | 0.31 | 5.7 | 7.1 | 8.1 |
| 0.05 | Cmpd. | Ex. 11 | 1245 | 1155 | 1080 | 0.27 | 0.38 | 0.56 | 5.9 | 7.4 | 8.5 |

*Antioxidant A is neopentanetetrayl tetrakis-[3-(3',5'-di-tert.-butyl-4'-hydroxyphenyl) propionate]
**Melt flow rate
***Yellowness Index

EXAMPLE 18

Process Stability of Polypropylene at 260° C.

Following the general procedure of Example 17, the instant phosphite of Example 16a was added to polypropylene containing 0.1% calcium stearate, but no phenolic antioxidant. As can be seen from the data given on Table 2, the instant phosphite exhibited excellent stabilization efficacy when used as the sole stabilizer in polypropylene.

TABLE 2

| % Additive | (psi) Transducer Pressure After Ext. | | | MFR (g/10 min) After Ext. | | | YI Color After Extrusion | | |
|---|---|---|---|---|---|---|---|---|---|
| | 1 | 3 | 5 | 1 | 3 | 5 | 1 | 3 | 5 |
| None* | 375 | 270 | 180 | 5.8 | 10.9 | 18.9 | 4.3 | 5.1 | 5.7 |
| 0.1 Compound Example 16a | 480 | 465 | 435 | 2.6 | 4.1 | 4.2 | 4.8 | 5.3 | 5.6 |

*Base formulation is Profax 6501 with 0.1% by weight of calcium stearate.

What is claimed is:

1. A 1,1'-biphenyl-2,2'-diyl phosphite of the formula

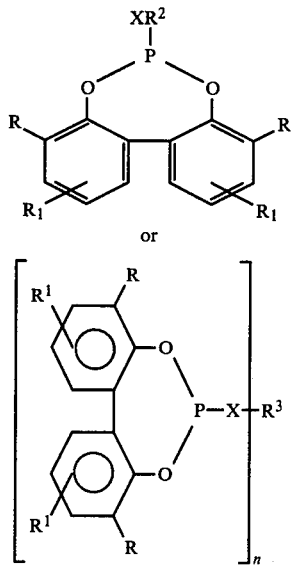

wherein
R is an alkyl group of 1 to 18 carbon atoms,
$R^1$ is hydrogen or alkyl group of 1 to 18 carbon atoms, and
$R^2$ is an alkyl group of 1 to 20 carbon atoms, phenyl, phenyl substituted by 1 to 3 alkyl groups each having 1 to 8 carbon atoms, or by two alkyl groups each having 1 to 8 carbon atoms and by $-COOR^4$ where $R^4$ is alkyl of 1 to 18 carbon atoms,
$R^3$ is an n-valent radical selected from the group consisting of a straight- or branched-chain alkylene of 2 to 12 atoms, a straight- or branched chain alkane-triyl, -tetrayl, -pentayl or -hexayl of 3 to 6 carbon atoms, alkylene of 4 to 6 carbon atoms, cycloalkylene of 6 to 12 carbon atoms, 1,4-cyclohexanedimethylene, arylene or arylene or arenetriyl of 6 to 10 carbon atoms, p-xylylene, phenylene-E-phenylene where E is a direct bond, $-O-$, $-S-$, $-NR^5-$, where $R^5$ is alkyl of 1 to 18 carbon atoms; a straight- or branched chain alkylene or alkylidene of 1 to 12 carbon atoms or cycloalkylidene of 5 to 6 carbon atoms, said arylene or said phenylene-E-phenylene substituted by 1 to 4 alkyl groups each having 1 to 8 carbon atoms, $-(CH_2)_xX(CH_2)_x$ where x is 2 to 6, dipentaerythrityl, and $$-(CH_2CHO)_zCH_2CH- \atop \phantom{-(CH_2CHO)_z}\, Y \phantom{CH_2C} Y$$

where
Y is hydrogen, methyl or ethyl and z is 1 to 10,
X is oxygen or sulfur, and n is 2 to 6.

2. A compound of claim 1 wherein
R is an α-branched alkyl radical of 3 to 8 carbon atoms, and
$R^1$ is an alkyl of 1 to 8 carbon atoms.

3. A compound of claim 2 wherein
$R^1$ is in the meta position to R group.

4. A compound of claim 3 wherein
R is tert-butyl or tert-octyl,
$R^1$ is a tert-alkyl group of 4 to 8 carbon atoms,
$R^2$ is phenyl substituted in the ortho positions by two alkyl groups each having 3 to 8 carbon atoms and in the para-positions by $-COOR^4$ where $R^4$ is alkyl of 1 to 12 carbon atoms.

5. A compound of claim 4 wherein $R^2$ is substituted in the ortho positions by two tert-butyl groups and in the para position by carbomethoxy where $R^4$ is methyl.

6. A compound of claim 1 wherein $R^3$ is alkylene of 2 to 6 carbon atoms, 1,2,3-propanetriyl, 2,2-dimethyl-1,2,2-propanetriyl, pentaerythrityl, 1,4-cyclohexylene, 1,4-cyclohexanedimethylene, 1,4-phenylene, phenylene-E-phenylene where E is methylene, 2,2-propylidene or 1,1-butylidene, 3-thiapentamethylene or

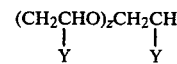

where Y is hydrogen or methyl and z is 1 to 3.

7. The compound of claim 1 which is O,O'-hexamethylene-bis[$O^1,O^2$-(3,3',5,5'-tetra-tert-butyl-1,1'-biphenyl-2,2'-diyl)phosphite].

8. The compound of claim 1 which is O,O'-neopentanediyl-bis[$O^1,O^2$-(3,3',5,5'-tetra-tert-butyl-1,1'-biphenyl-2,2'-diyl)phosphite].

* * * * *